United States Patent
Imahashi et al.

(10) Patent No.: US 8,066,643 B2
(45) Date of Patent: Nov. 29, 2011

(54) ULTRASONIC ENDOSCOPE

(75) Inventors: Takuya Imahashi, Kawasaki (JP);
Akiko Mizunuma, Tokyo (JP);
Yukihiko Sawada, Yoshikawa (JP);
Katsuhiro Wakabayashi, Tokyo (JP);
Sunao Sato, Tokyo (JP)

(73) Assignee: Olympus Corporation, Tokyo (JP)

( * ) Notice: Subject to any disclaimer, the term of this patent is extended or adjusted under 35 U.S.C. 154(b) by 845 days.

(21) Appl. No.: 11/666,779

(22) PCT Filed: Oct. 4, 2005

(86) PCT No.: PCT/JP2005/018317
§ 371 (c)(1),
(2), (4) Date: May 1, 2007

(87) PCT Pub. No.: WO2006/051659
PCT Pub. Date: May 18, 2006

(65) Prior Publication Data
US 2008/0200814 A1 Aug. 21, 2008

(30) Foreign Application Priority Data
Nov. 9, 2004 (JP) .................................. 2004-325248

(51) Int. Cl.
*A61B 8/00* (2006.01)
(52) U.S. Cl. ...................................................... 600/459
(58) Field of Classification Search .................. 600/459; 310/311
See application file for complete search history.

(56) References Cited

U.S. PATENT DOCUMENTS

| | | | |
|---|---|---|---|
| 5,685,311 A * | 11/1997 | Hara ............................. | 600/459 |
| 5,810,009 A | 9/1998 | Mine et al. | |
| 5,857,974 A | 1/1999 | Eberle et al. | |
| 6,468,221 B2 * | 10/2002 | Ohara et al. ................... | 600/462 |
| 7,400,079 B2 * | 7/2008 | Omura et al. ................... | 310/355 |

FOREIGN PATENT DOCUMENTS

| | | |
|---|---|---|
| EP | 1 795 132 A1 | 6/2007 |
| JP | 02-116358 | 5/1990 |
| JP | 10-192281 | 7/1998 |
| JP | 2001-314406 | 11/2001 |
| JP | 2003-033353 | 2/2003 |
| JP | 2004-298240 | 10/2004 |

* cited by examiner

Primary Examiner — Jacqueline Cheng
(74) Attorney, Agent, or Firm — Scully, Scott, Murphy & Presser, P.C.

(57) ABSTRACT

The present invention provides an ultrasonic endoscope, comprising: an ultrasonic transducer in a cylindrical shape including a plurality of piezoelectric devices, an acoustic matching layer stacked on a principal plane on a sound emitting plane side, an acoustic lens on a plane of the acoustic matching layer opposite to a plane facing the piezoelectric devices, and a backing material stacked on another principal planes of the piezoelectric devices; an endoscopic observation and endo-therapy unit provided, for performing endoscopic image observation, at a proximal end side of the ultrasonic transducer; a cable assembly including a plurality of cables for transmitting signals to and from the ultrasonic transducer. In the above configuration, the cable assembly is arranged in such a manner that the cable assembly passes through an inside portion of the ultrasonic transducer, and is connected to the ultrasonic transducer at a distal end side of the ultrasonic transducer. Thereby, an ultrasonic endoscope is provided that has an ultrasonic transducer in which the ultrasonic transducer and coaxial cables will not be disconnected even under thermal or mechanical loads.

4 Claims, 11 Drawing Sheets

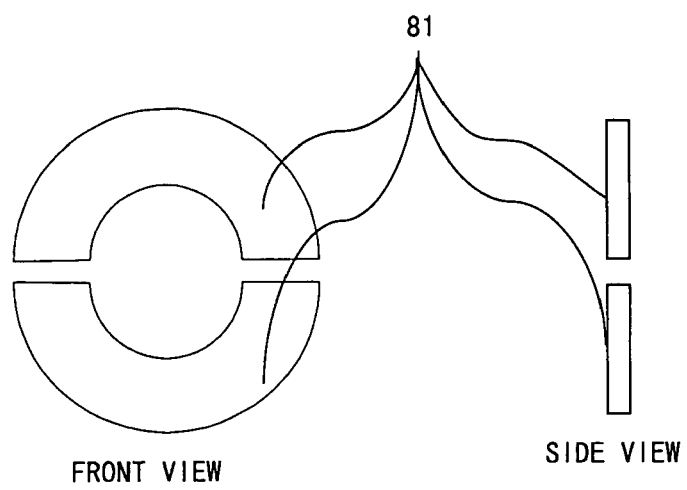
FRONT VIEW   SIDE VIEW
F I G. 8

ULTRASONIC ENDOSCOPE

TECHNICAL FIELD

The present invention relates to an electronic radial scanning ultrasonic endoscope, and particularly to a method of connecting coaxial cables for transmitting signals and an ultrasonic transducer in which a plurality of transducer elements are arranged in such a manner that the arranged transducer elements to the cylindrical shape along the periphery of the ultrasonic transducer.

BACKGROUND ART

There are two conventional methods of radial scanning ultrasonic endoscopes, the electronic scanning method that performs electronic scans and the mechanical scanning method that performs mechanical scans. In the ultrasonic endoscopes of the electronic scanning method, the configuration is generally employed in which the ultrasonic transducer formed in a cylindrical shape for performing the radial scan and the endoscopic observation and endo-therapy units for performing endoscopic image observation are arranged in very close proximity to each other and are fixed as one piece, and a plurality of flexible printed circuit (FPC) boards are used as cables for transmitting electric signals to and from the ultrasonic transducer.

In addition, a plurality of FPC boards connected to the transducer elements are arranged in such a manner that an arch is formed by the plurality of FPC boards in order to avoid being close to the endoscopic observation and endo-therapy units such as its instrument channel port and the like, and thereafter the plurality of FPC boards are connected to signal cables (coaxial cables) at a spot closer to the proximal end than the bending section of the endoscope (on the side of the control section of the ultrasonic endoscope body) (see Patent Document 1, for example).

In the ultrasonic endoscopes of the mechanical scanning method, a scan is performed by turning one ultrasonic transducer in the insertion axis direction using an electric motor or the like provided at the proximal end. Accordingly, the ultrasonic transducer is attached by means of a shaft bearing structure such as ball bearings provided in the vicinity of the ultrasonic transducer (see Patent Document 2, for example).
Patent Document 1
Japanese Patent Application Publication No. 2001-314406
Patent Document 2
Japanese Patent Application Publication No. 2-116358

DISCLOSURE OF THE INVENTION

The ultrasonic endoscope of the electronic scanning method has the problem that when the FPC boards and the coaxial cables are connected and the components for the cables are inserted into the insertion tube, tensile force applied in the direction of the control section tends to break the connection between the ultrasonic transducer and the FPC boards, which results in disconnection.

Also, because the FPC boards, which are naturally flat shaped, are curved to form an arch, the residual stress of the FPC boards varies with thermal variations and variations in atmospheric pressure during sterilization and disinfection, and the FPC boards tend to change their shape, causing an increased likelihood of disconnection between the ultrasonic transducer and the connection portions in the FPC boards and between the cables and the connection portions in the FPC boards, which is problematic.

Also, the cross section of the FPC board is rectangular while the cross section of the ultrasonic endoscope is circular; accordingly, there is the problem that spatial losses result, requiring larger diameter of the ultrasonic endoscope even when the FPC boards are packed together into the insertion tube.

Also, there is the problem that, because the connection portions are at a place that is closer to the control section than to the bending section, it is difficult to repair when a disconnection is caused in this configuration.

Also, in the ultrasonic endoscope of the mechanical scanning method, the interval between the axis of an endoscopic image and the acoustic axis emitted from the ultrasonic transducer is determined by the dimension (diameter) of the ultrasonic transducer and the structure of the shaft bearing in the vicinity of the ultrasonic transducer. The diameter of the ultrasonic transducer influences the penetration, which in turn influences ultrasonic images; thus, the diameter of the ultrasonic transducer is required to be at least approximately 10 mm. Additionally, the structure is conventionally required to be the bearing structure; accordingly, the interval between the endoscopic image and the acoustic axis is approximately 10 mm. Thus, it is difficult to make images of surfaces of the body cavities that are in endoscopic images correspond to ultrasonic images (cross section images) of inside portions of the corresponding area on the endoscopic surfaces of the body cavities, which is problematic.

The present invention is achieved in view of the above problems, and it is an object of the present invention to provide an ultrasonic endoscope having an ultrasonic transducer in which the ultrasonic transducer and coaxial cables will not become disconnected even under thermal or mechanical loads.

In addition, it is another object of the present invention to provide an ultrasonic endoscope in which the length of the rigid portion required as a space for wiring is shortened as much as possible.

The present invention employs the configurations as described below in order to solve the above problems.

According to one aspect of the present invention, an ultrasonic endoscope according to the present invention is an ultrasonic endoscope comprising: an ultrasonic transducer in a cylindrical shape including a plurality of piezoelectric devices, an acoustic matching layer stacked on a principal plane on a sound emitting plane side, an acoustic lens on a plane of the acoustic matching layer opposite to a plane facing the piezoelectric devices, and a backing material stacked on another principal planes of the piezoelectric devices; an endoscopic observation and endo-therapy units provided, for performing endoscopic image observation, at the proximal end side of the ultrasonic transducer; a cable assembly (a bundle of cable) including a plurality of cables for transmitting signals to and from the ultrasonic transducer, in which: the cable assembly is arranged in such a manner that the cable assembly passes through an inside portion of the ultrasonic transducer and is connected to the ultrasonic transducer at the distal end side of the ultrasonic transducer.

Also, it is desirable in an ultrasonic endoscope according to the present invention that the ultrasonic transducer includes a ring-shaped frame member in an inside portion of the distal end side for forming the cylindrical shape; the ultrasonic endoscope further includes a ring-shaped circuit board having an outer diameter that is greater than the inner diameter of the frame member and that is smaller than the inner diameter of the ultrasonic transducer, the ring-shaped circuit board being for connecting respective cables included in the cable assembly to the ultrasonic transducer; and the circuit board be locked in the frame member at the distal end side of the ultrasonic transducer.

Also, it is desirable in an ultrasonic endoscope according to the present invention that the ultrasonic transducer includes a ring-shaped frame member in an inside portion of the distal end side for forming the cylindrical shape; and the ultrasonic endoscope further comprises: a ring-shaped circuit board having an outer diameter that is smaller than the inner diameter of the frame member, the ring-shaped circuit board being for connecting respective cables included in the cable assembly to the ultrasonic transducer; and a locking member for locking the circuit board in the frame member at the distal end side of the ultrasonic transducer.

Also, it is desirable in an ultrasonic endoscope according to the present invention that, for the ultrasonic endoscope according to claim 1, the ultrasonic endoscope further comprises a balloon unit for covering the ultrasonic transducer; and the balloon unit or the acoustic lens be arranged in such a manner that the acoustic axis of ultrasound emitted from the acoustic lens and the balloon unit are not orthogonal to each other.

BRIEF DESCRIPTION OF THE DRAWINGS

FIG. 8 shows locking members in an example of a variation of the ultrasonic transducer;

BEST MODES FOR CARRYING OUT THE INVENTION

Figure 1:
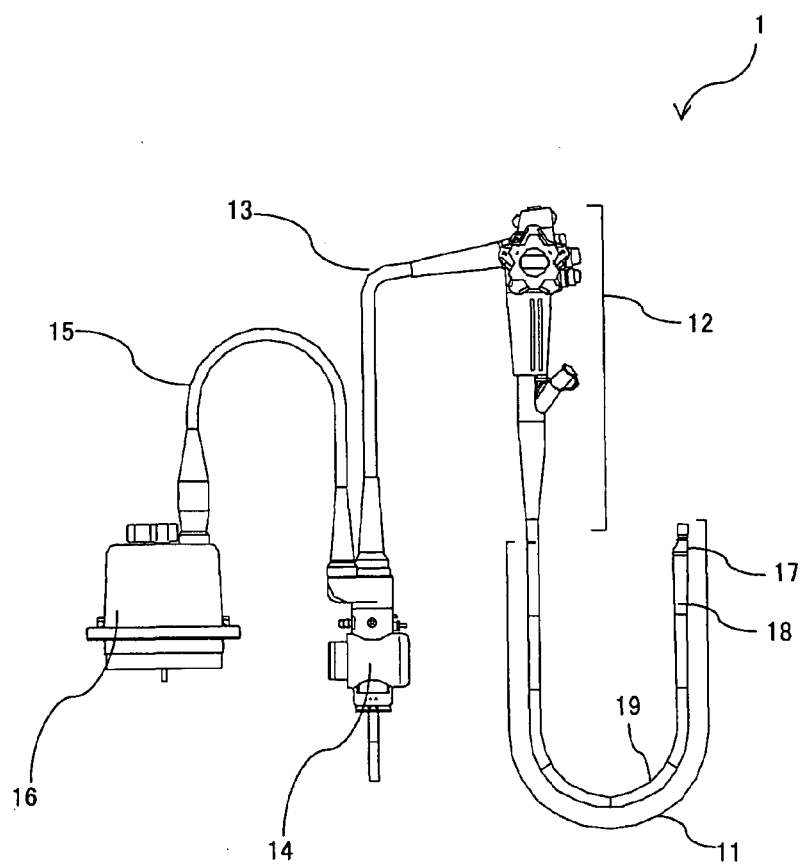
FIG. 1 shows a configuration of the entire ultrasonic endoscope.

Hereinafter, embodiments of the present invention will be described by referring to the drawings.

FIG. 1 shows a configuration of an entire ultrasonic endoscope.

In FIG. 1, an ultrasonic endoscope 1 comprises an insertion section 11 that is to be inserted into body cavities, a control section 12 connected to a proximal end side of the insertion section 11, and a universal code 13 that extends from a side surface of the control section 12.

A scope connector 14 that is connected to a light source unit (not shown) for providing illumination light is connected to the proximal end of the universal code 13. An ultrasonic code 15 has an ultrasonic connector 16 that is electrically connected to a diagnostic ultrasound system (not shown) and that is for driving an ultrasonic transducer and creating ultrasonic diagnosis images by performing various signal processes on received signals. The ultrasonic code 15 extends from the scope connector 14.

The insertion section 11 comprises, in the order starting from the distal end side thereof and in a connected state, a rigid tip portion 17 made of a stiff material, a bending section 18 that is at the proximal end side of the rigid tip portion 17 and that can arbitrarily bend, and a insertion tube 19 that is at the proximal end side of the bending section 18, is connected to the distal end side of the control section 12, and is elongate and flexible.

Figure 2:
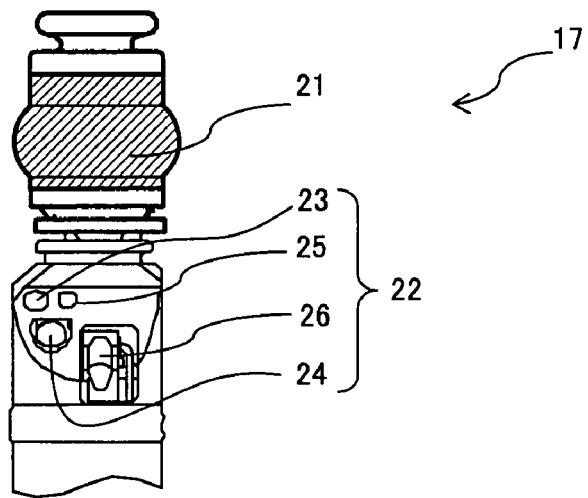
FIG. 2 shows a configuration of the rigid tip portion.

FIG. 2 shows a configuration of the rigid tip portion.

In FIG. 2, the rigid tip portion 17 comprises an endoscopic observation and endo-therapy unit 22 for directly performing endoscopic image observation of surfaces of tissues of diseased area, and an ultrasonic transducer 21 for emitting ultrasound in order to receive the ultrasound that have been reflected from the acoustic impedance boundary in the tissues of diseased area that are the observation area.

The endoscopic observation and endo-therapy unit 22 comprises an illumination lens 23 for guiding the illumination light to the surfaces of the tissues of diseased area, an objective lens 24 for condensing the light reflected from the surfaces of the tissues of diseased area, an nozzle 25 for feeding gas or liquid to body cavities, and an instrument channel outlet 26 for suction the gas or liquid in the body cavities and accepting an instrument.

Figure 3:
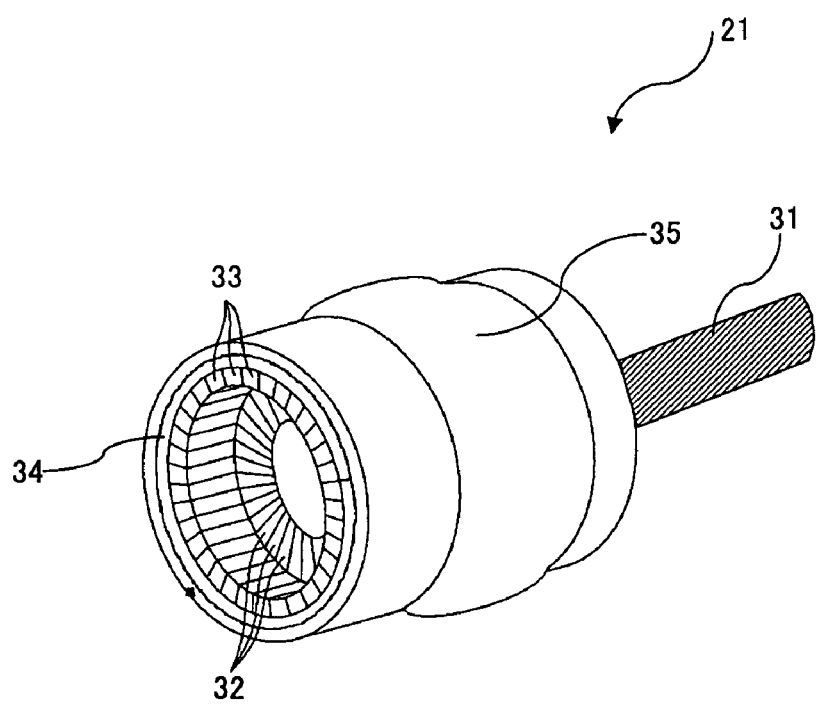
FIG. 3 shows a configuration of the ultrasonic transducer.

FIG. 3 shows a configuration of the ultrasonic transducer.

In FIG. 3, the ultrasonic transducer 21 comprises circuit boards 32 connected to a cable assembly 31 that includes a plurality of cables for the transmission of electric signals to and from an ultrasonic endoscope body via the bending section 18 and the insertion tube 19, boards 33 connected to the circuit boards 32 and linked to a cylindrical piezoelectric device for emitting ultrasound (see FIG. 4), an acoustic matching layer 34 formed on the outer surfaces of the piezoelectric devices for protecting the piezoelectric devices and for performing acoustic matching with an external environment, an acoustic lens 35 formed on the outer surface of the acoustic matching layer 34 for condensing the ultrasound transmitted from the piezoelectric devices, and a backing material (see FIG. 4) on the inner surfaces of the piezoelectric devices. The ultrasonic transducer 21 is cylindrical.

Figure 4:
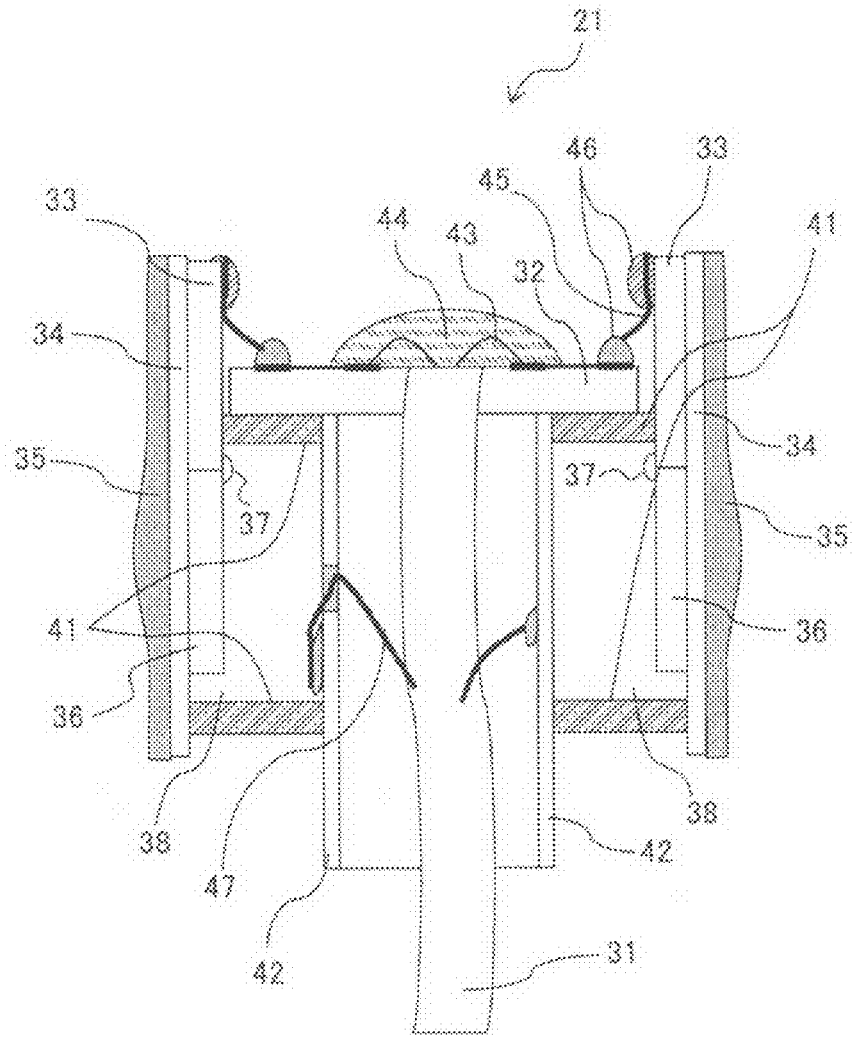
FIG. 4 shows an internal configuration of the ultrasonic transducer.

FIG. 4 shows an internal configuration of the ultrasonic transducer.

In FIG. 4, the ultrasonic transducer 21 comprises the circuit boards 32 connected to the cable assembly 31, the boards 33, piezoelectric devices 36, the acoustic matching layer 34 stacked on the outer surface of the piezoelectric devices 36, the acoustic lens 35 stacked on the outer surface of the acoustic matching layer 34, and a backing material 38 on the inner surfaces of the piezoelectric devices 36.

The cable assembly 31 and the circuit boards 32 are connected to each other via cables 43, and the connection spots between them are covered by a potting material 44. The circuit boards 32 and the boards 33 are connected to each other via wires 45 at soldered portions 46, and the boards 33 are connected to the piezoelectric devices 36 via connection units 37. Thereby, electric signals are transmitted to the piezoelectric devices 36.

A cylindrical nose piece 42 surrounding the cable assembly 31 is provided to the circuit boards 32, and the circuit boards 32 are partially grounded via a ground line 47 in the cylindrical nose piece 42. The circuit boards 32 are locked in ring-shaped frame members 41 in such a way that the piezoelectric devices 36, the boards 33, the acoustic matching layer 34, the acoustic lens 35, and the backing material 38 form a cylindrical shape.

The boards 33 have electric conductivity on one surface, and have electric non-conductance on the other surface. In FIG. 4, the surface contacting the soldered portions 46 has electric conductivity; and the surface contacting the acoustic matching layer 34 has electric non-conductance.

In order to drive the piezoelectric devices 36, it is necessary that the piezo devices 36 are electrically connected to the cable assembly 31, and in FIG. 4, the piezoelectric devices 36 and the cable assembly 31 are electrically connected via the circuit boards 32, the wires 45, and the connection units 37. By not directly connecting the piezoelectric devices 36 and the cable assembly 31 but by indirectly connecting the piezoelectric devices 36 and the cable assembly 31 via the circuit boards 32 or boards 33, the risk of disconnection at the time of deforming the ultrasonic endoscope can be reduced.

Next, processes of manufacturing the ultrasonic transducer 21 are explained.

Figure 5:
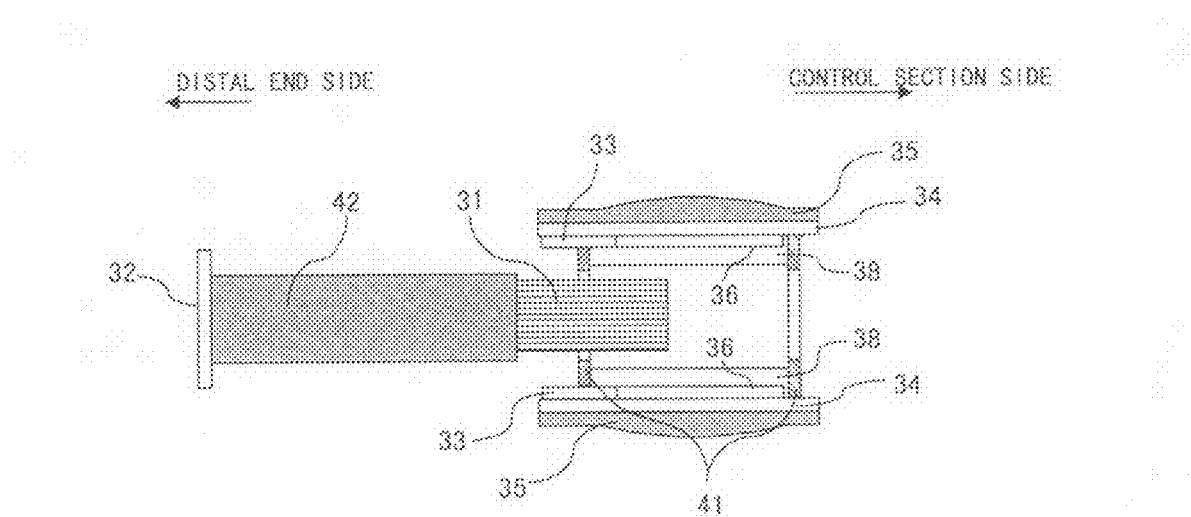
FIG. 5 is a first view showing processes of manufacturing the ultrasonic transducer.

First, as shown in FIG. 5, the cable assembly 31 and the circuit boards 32 are connected to each other, and the portion of the cable assembly 31 closer to the circuit boards 32 is surrounded by the nose piece 42. The portion of the cable assembly closer to the ultrasonic endoscope body is inserted, from the distal end side of the ultrasonic endoscope, into a cylinder made by stacking the backing material 38, the boards 33, the piezoelectric devices 36, the acoustic matching layer 34, and the acoustic lens 35.

Figure 6:
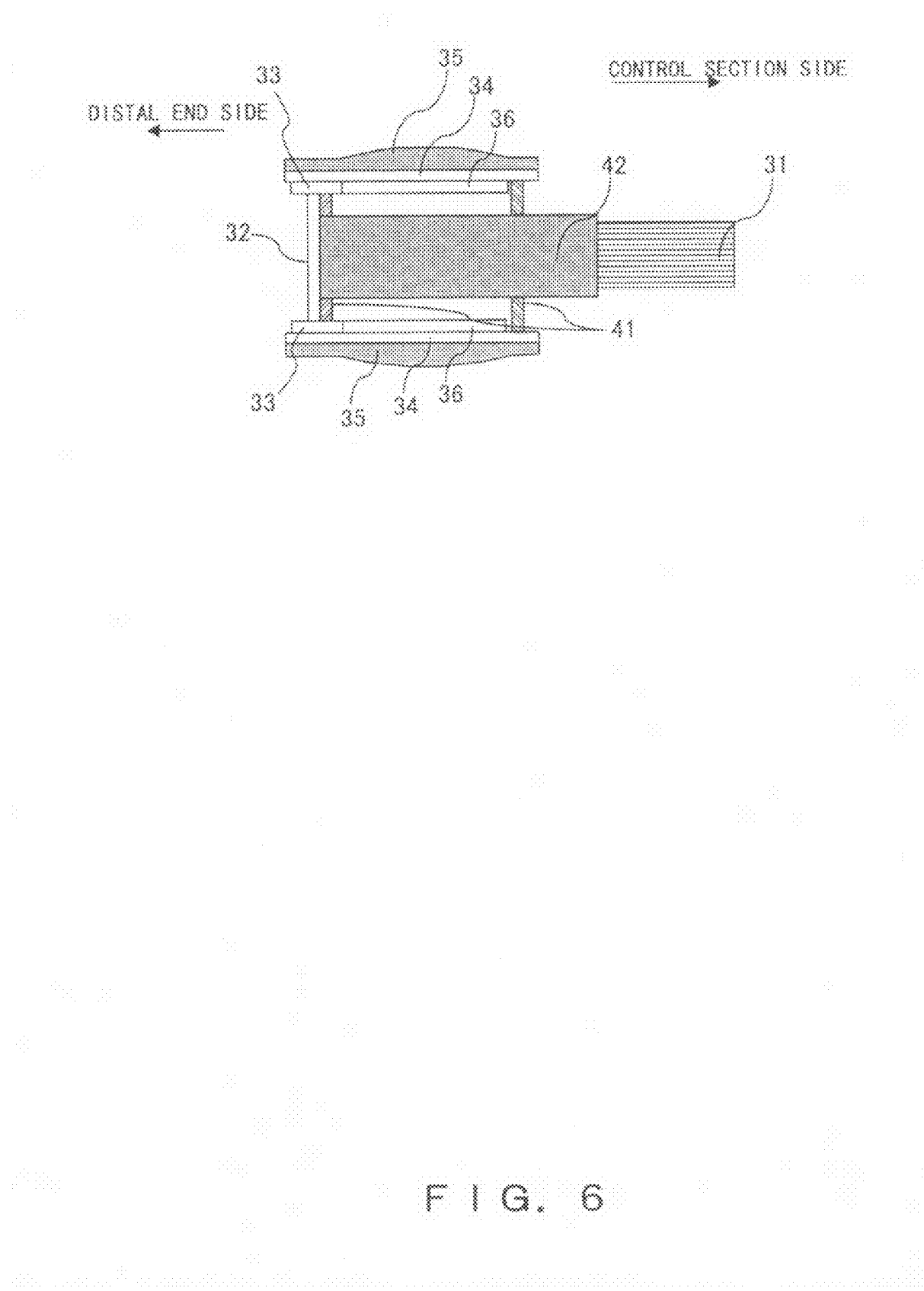
FIG. 6 is a second view showing processes of manufacturing the ultrasonic transducer.

Then, as shown in FIG. 6, the circuit boards 32 are fixed to the frame member 41 that is closer to the distal end of the ultrasonic endoscope. In this configuration, the outer diameter of the entire set of circuit boards 32 arranged in a ring shape is greater than the inner diameter of the frame members 41, and is smaller than the inner diameter of the ultrasonic transducer 21, i.e., is smaller than the inner diameter of the backing material 38.

Next, variations in the ultrasonic transducer and its manufacturing processes will be explained.

In this present variation example, the circuit boards 32 are not locked in the ring-shaped frame member 41, but are locked by using the members that are used for locking the circuit boards 32. This contrasts with the above embodiment.

Figure 7:
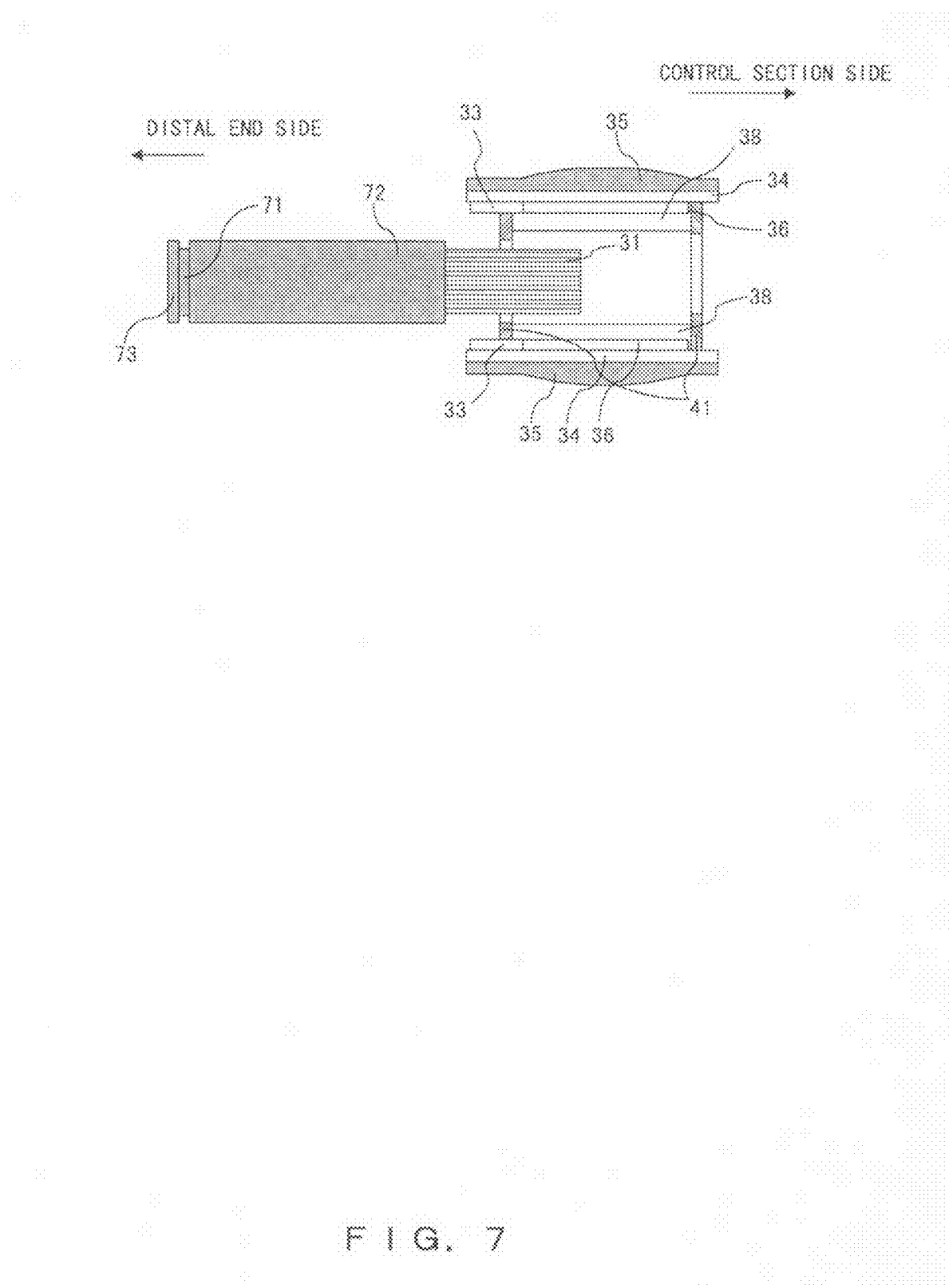
FIG. 7 is a first view showing processes of manufacturing the ultrasonic transducer in an example of a variation.

First, as shown in FIG. 7, the cable assembly 31 and a circuit board 73 are connected to each other, and the portion of the cable assembly 31 closer to the circuit board 73 is surrounded by a nose piece 72. This nose piece 72 has a trench 71. Next, in a similar manner to the above embodiment, the portion of the cable assembly 31 closer to the ultrasonic endoscope body is inserted, from the distal end side of the ultrasonic endoscope, into a cylinder made by stacking the backing material 38, the boards 33, the piezoelectric devices 36, the acoustic matching layer 34, and the acoustic lens 35.

Figure 9:
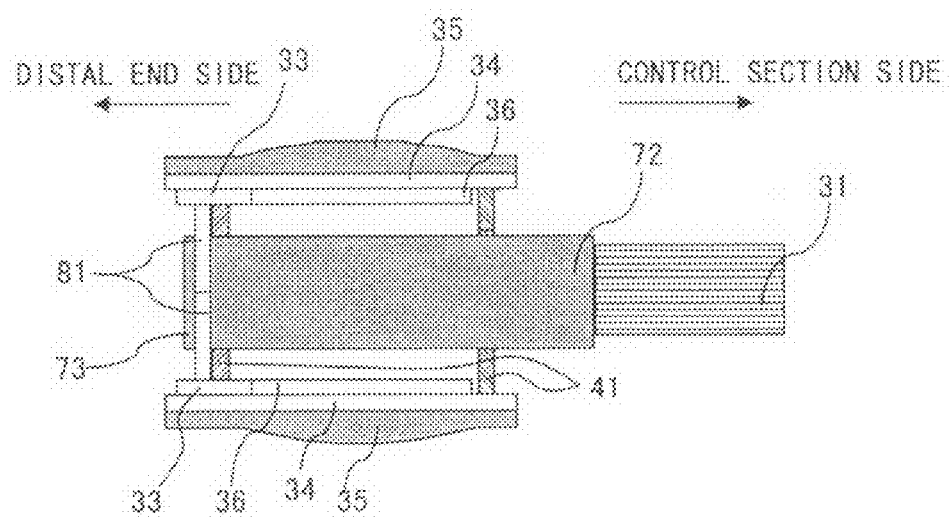
FIG. 9 is a second view showing processes of manufacturing the ultrasonic transducer in an example of a variation.
Figure 10:
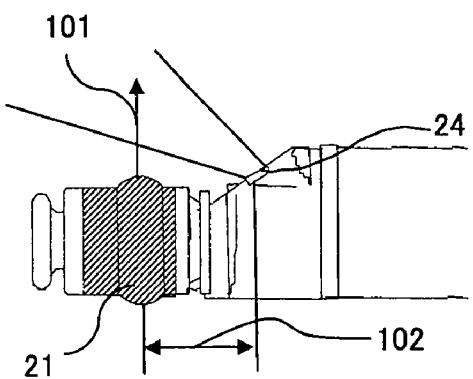
FIG. 10 shows a positional relationship between the objective lens and the acoustic axis.

Then, as shown in FIG. 8, locking members 81 are fitted into the trench 71, and the circuit board 73 is fixed to the frame member 41 that is closer to the distal end of the ultrasonic endoscope by using the locking members 81 as shown in FIG. 9. In this configuration, the outer diameter of the circuit board 73, which has a ring shape, is smaller than the inner diameter of the above ultrasonic transducer 21, i.e., is smaller than the inner diameter of the backing material 38, and is smaller than the inner diameter of the frame members 41. However, the circuit board 73 is fixed to the ring-shaped frame members 41 by the locking members 81 that are fitted into the trench 71.

As described above, the cable assembly 31 is formed by grouping a plurality of cables for the transmission of electric signals via the bending section 18 and the insertion tube 19; accordingly, the sectional area of the cable assembly 31 can be minimized. Further, the cable assembly 31 is inserted, from the distal end side of the ultrasonic endoscope, into the inside portion of the backing material 38 that is one of the materials stacked in a cylindrical shape, and is connected to the circuit boards 32 at the distal end side of the ultrasonic endoscope. Accordingly, the cable assembly 31 can be thinner on the portion closer to the control section 12 than on the portion closer to the distal end of the ultrasonic endoscope. In addition, there will not be an unnecessary load on the connection point between the cable assembly 31 and the circuit boards 32 when manufacturing the ultrasonic transducer 21.

Because the cable assembly 31 is connected to the circuit boards 32 at a position closer to the distal end of the ultrasonic endoscope and inside the backing material 38, which is one of the materials stacked in a cylindrical shape so that bearing members can be dispensed with, the interval 102 between an acoustic axis 101 representing the direction in which the ultrasound emitted from the ultrasonic transducer 21 travel and the objective lens 24 can be shortened. Further, it is also possible to shorten rigid length of the rigid tip portion 17 that is inserted into body cavities.

Figure 11:
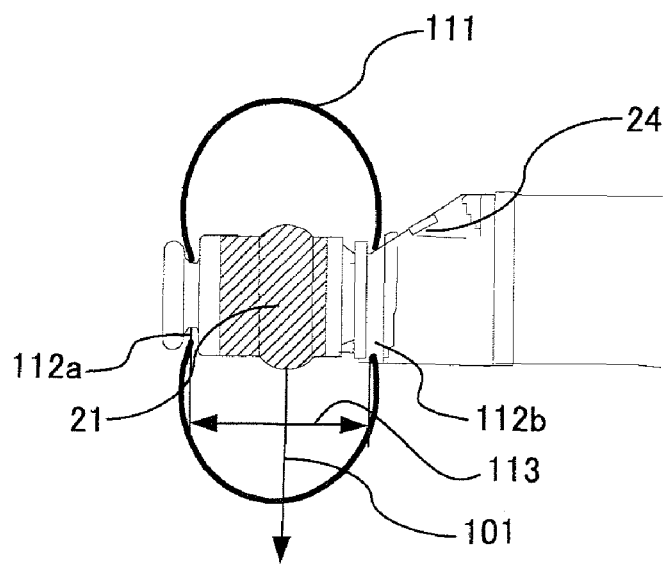
FIG. 11 shows a positional relationship between a balloon unit and the acoustic axis.

Also, the cable assembly 31 is connected to the circuit board 32 inside the backing material 38, which is one of the materials stacked in a cylindrical shape, and at the distal end side of the ultrasonic endoscope when a balloon unit 111 for covering the ultrasonic transducer 21 is attached to balloon attachment grooves 112a and 112b; accordingly, it is possible, as shown in FIG. 11, to prevent an acoustic axis 101 from being at the midpoint of the interval 113 between the balloon attachment grooves 112a and 112b, and to prevent the acoustic axis 101 from being orthogonal to the wall of the balloon unit 111 when the balloon unit 111 is in an inflated state. This configuration contributes to the reduction of multiple echoes.

In the above, the embodiments of the present invention have been explained by referring to the drawings. However, the scope of the present invention is not limited to the above embodiments, and various alterations, modifications, and the like are allowed without departing from the spirit of the present invention.

According to the present invention, a bearing structure is dispensed with, and the ultrasonic transducer and the coaxial cables are connected at the tip portion of the insertion tube of the ultrasonic endoscope. Accordingly, it is also possible to shorten the length of the rigid portion of the ultrasonic endoscope's tip portion, which is inserted into body cavities, thus realizing an ultrasonic endoscope that causes less discomfort in patients.

In addition, according to the present invention, the ultrasonic transducer and the coaxial cables are connected to each other at the tip portion of the insertion tube of the ultrasonic endoscope; accordingly, an acoustic lens for converting ultrasound can be arranged on the control section side of the tip portion of the ultrasonic endoscope, and thus it is possible to prevent the directions of the ultrasound transmitted and received from and by the acoustic lens from being orthogonal to the balloon unit. Thereby, multiple reflection caused by the balloon unit can be reduced.

The invention claimed is:
1. An ultrasonic endoscope comprising:
an ultrasonic transducer in a cylindrical shape including a plurality of piezoelectric devices, an acoustic matching layer stacked on a principal plane on a sound emitting plane side, an acoustic lens on a plane of the acoustic matching layer opposite to a plane facing the piezoelectric devices, and a backing material stacked on another principal plane of the piezoelectric devices;
an endoscopic observation and endo-therapy unit provided, for performing endoscopic image observation, at a proximal end side of the ultrasonic transducer;

a cable assembly formed by grouping a plurality of cables for transmitting signals to and from the ultrasonic transducer, wherein:

the cable assembly is arranged in such a manner that the cable assembly passes through an inside portion of the ultrasonic transducer and is connected to the ultrasonic transducer at a distal end side of the ultrasonic transducer; wherein the ultrasonic transducer includes a ring-shaped frame member in an inside portion of the distal end side for forming the cylindrical shape;

the ultrasonic endoscope further includes a ring-shaped circuit board having an outer diameter that is greater than an inner diameter of the frame member and that is smaller than an inner diameter of the ultrasonic transducer, for connecting respective cables included in the cable assembly to the ultrasonic transducer; and the circuit board is locked in the frame member at the distal end side of the ultrasonic transducer.

2. The ultrasonic endoscope according to claim 1, wherein:

the ultrasonic endoscope further comprises a balloon unit for covering the ultrasonic transducer; and the balloon unit or the acoustic lens is arranged in such a manner that the acoustic axis of ultrasound emitted from the acoustic lens and the balloon unit are not orthogonal to each other.

3. An ultrasonic endoscope comprising:

an ultrasonic transducer in a cylindrical shape including a plurality of piezoelectric devices, an acoustic matching layer stacked on a principal plane on a sound emitting plane side, an acoustic lens on a plane of the acoustic matching layer opposite to a plane facing the piezoelectric devices, and a backing material stacked on another principal plane of the piezoelectric devices;

an endoscopic observation and endo-therapy unit provided, for performing endoscopic image observation, at a proximal end side of the ultrasonic transducer;

a cable assembly formed by grouping a plurality of cables for transmitting signals to and from the ultrasonic transducer, wherein:

the cable assembly is arranged in such a manner that the cable assembly passes through an inside portion of the ultrasonic transducer and is connected to the ultrasonic transducer at a distal end side of the ultrasonic transducer; wherein the ultrasonic transducer includes a ring-shaped frame member in an inside portion of the distal end side for forming the cylindrical shape; and the ultrasonic endoscope further comprises:

a ring-shaped circuit board having an outer diameter that is smaller than an inner diameter of the frame member, for connecting respective cables included in the cable assembly to the ultrasonic transducer; and a locking member for locking the circuit board in the frame member at the distal end side of the ultrasonic transducer.

4. The ultrasonic endoscope according to claim 3, wherein:

the ultrasonic endoscope further comprises a balloon unit for covering the ultrasonic transducer; and the balloon unit or the acoustic lens is arranged in such a manner that the acoustic axis of ultrasound emitted from the acoustic lens and the balloon unit are not orthogonal to each other.

* * * * *